United States Patent [19]

Gu

[11] Patent Number: 4,847,428

[45] Date of Patent: Jul. 11, 1989

[54] PURIFICATION OF HALOGENATED AROMATIC COMPOUNDS

[75] Inventor: Jen-Tau Gu, Yuan-Ho, Taiwan

[73] Assignee: China Technical Consultants, Inc., Taipei, Taiwan

[21] Appl. No.: 121,973

[22] Filed: Nov. 18, 1987

[51] Int. Cl.$^4$ ............................................. C07C 41/01
[52] U.S. Cl. .................................................... 568/639
[58] Field of Search ......................................... 568/639

[56] References Cited

U.S. PATENT DOCUMENTS 4,214,103  7/1980  Garman et al. ..................... 568/639

FOREIGN PATENT DOCUMENTS 1472383  5/1977  United Kingdom ................ 568/639

*Primary Examiner*—Bruce D. Gray

*Attorney, Agent, or Firm*—Limbach, Limbach & Sutton

[57] ABSTRACT

A process for recrystallization of a brominated aromatic compound under pressure for purifying it from the contamination by bromine and hydrogen bromide, comprising the steps of: placing the brominated aromatic compound in a solvent or a combination of solvents selected from toluene, 1,dibromoethane, m-xylene, benzene, dichloromethane, chloroform, and 1,2-dichloroethane; adding into the resultant mixture a base or a combination of bases selected from pyridine, ethylene diamine, n-butylamine, tert-butylamaine, triethylamine, sodium ethoxide, sodium hydroxide, potassium hydroxide, sodium carbonate, and sodium bicarbonate; and heating the resultant mixture to a temperature above the atmospheric boiling point and at a pressure above the vapor pressure of the resultant material at that temperature.

4 Claims, 3 Drawing Sheets

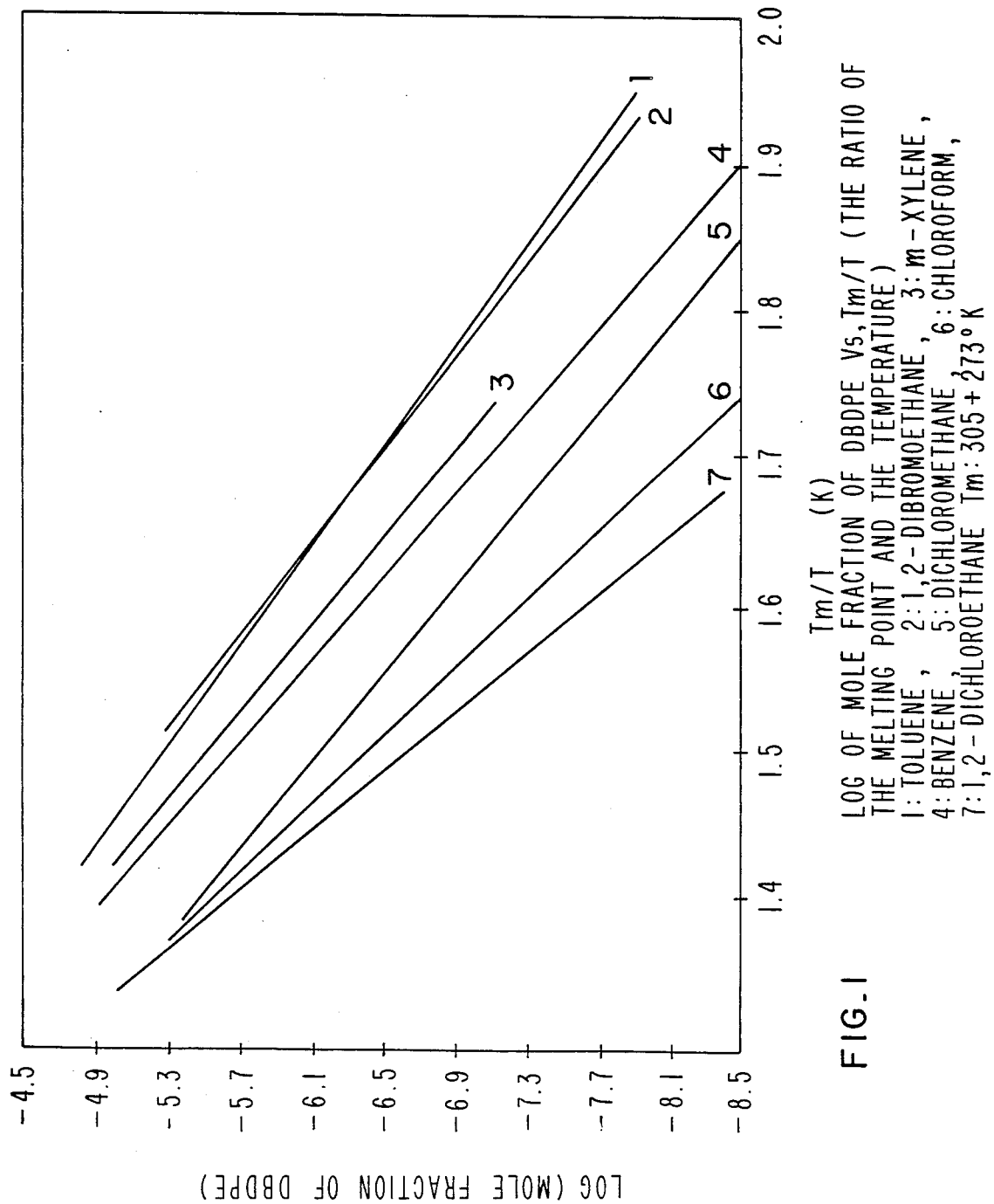

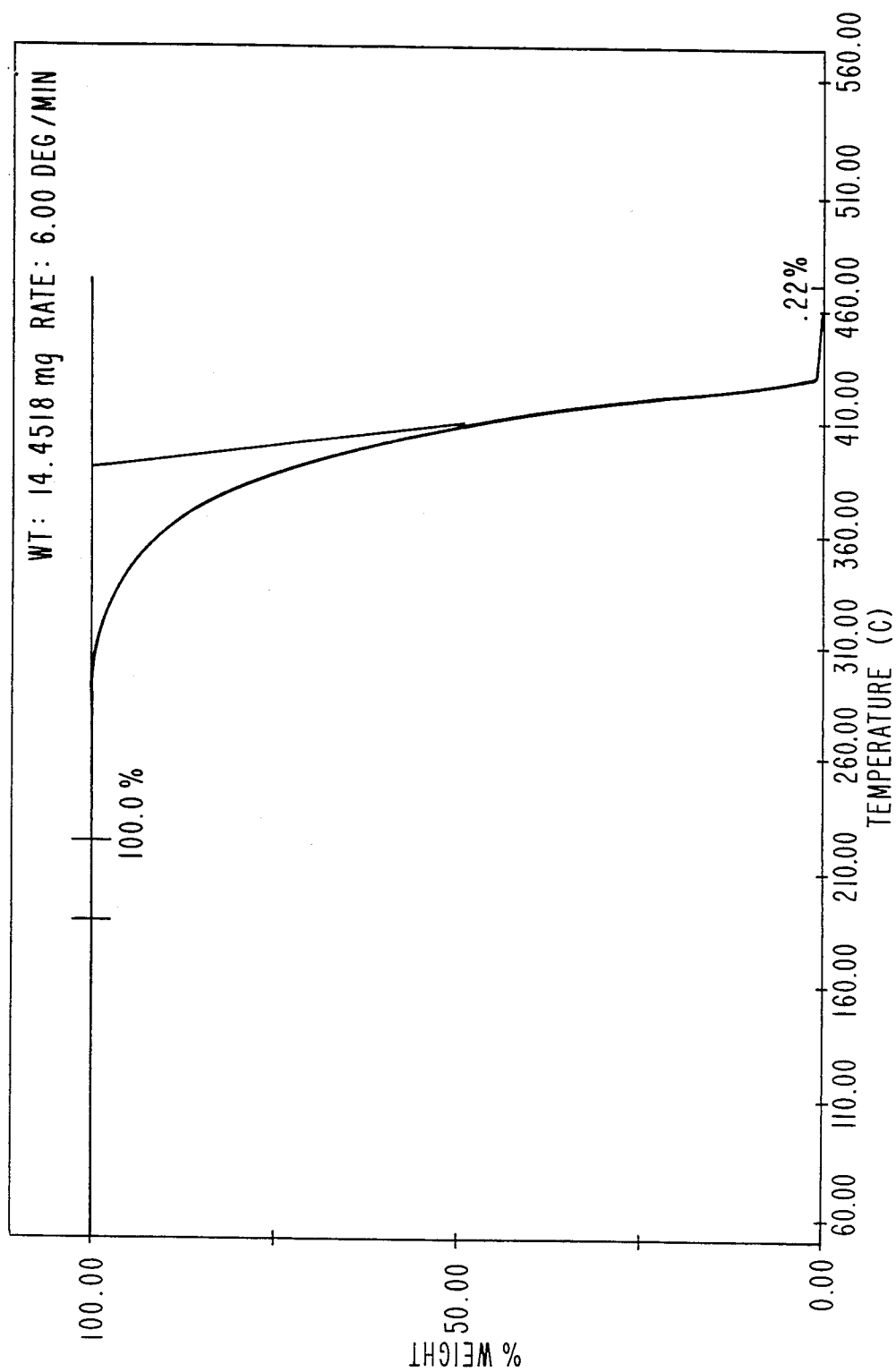
FIG. 2 THERMOGRAVIMETRIC ANALYSIS OF THE RECRYSTALLIZED PRODUCT (DBDPE) OF EXAMPLE 1

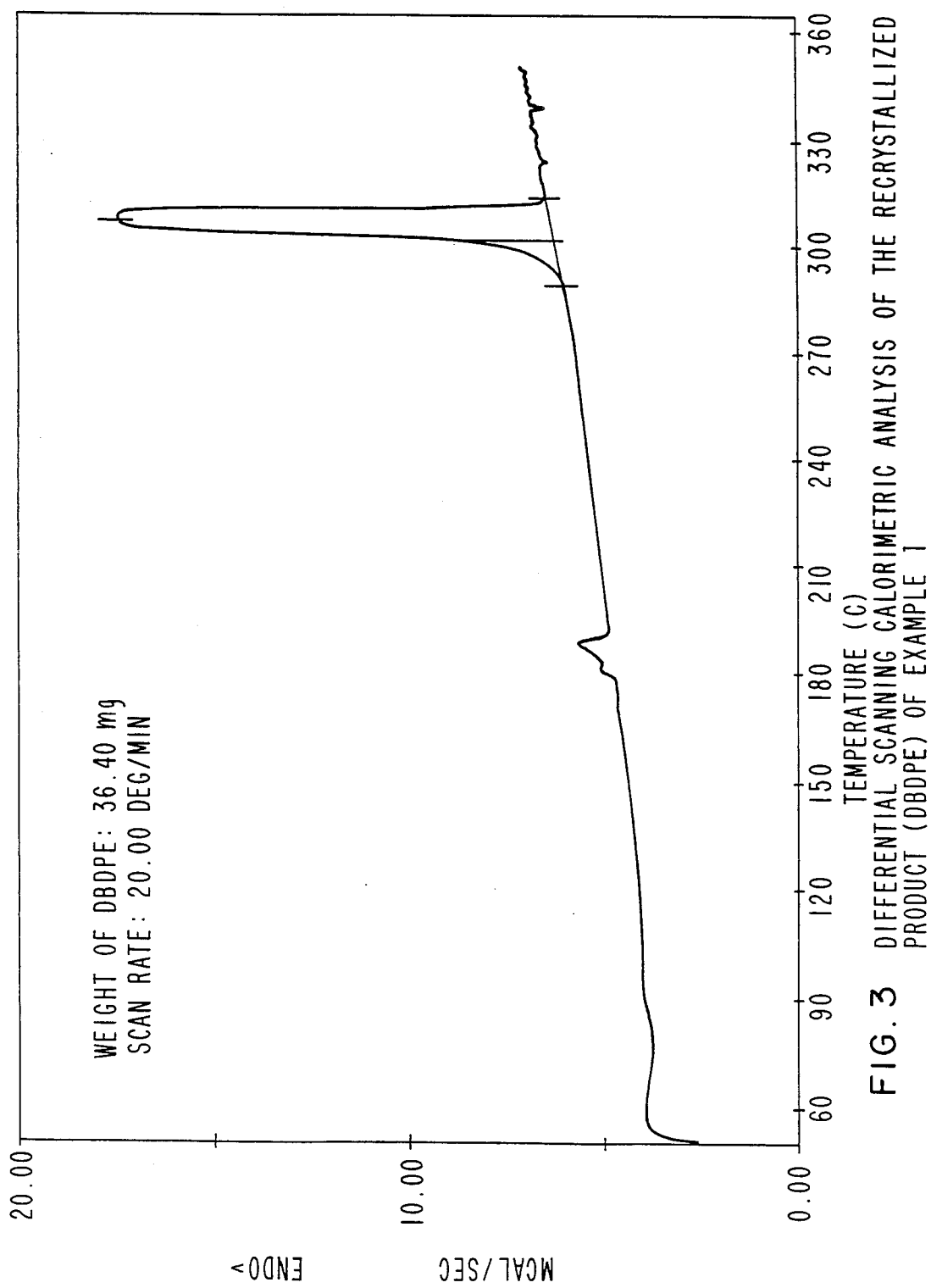

PURIFICATION OF HALOGENATED AROMATIC COMPOUNDS

BACKGROUND OF THE INVENTION

This invention relates to a process for purifying a halongenated aromatic compound, particularly to a process for purification of a brominated aromatic compound, such as decabromodiphenyl ether by recrystallization.

It is known that in the reaction of bromine with diphenyl ether in the presence of anhydrous aluminum chloride, the main product, decabromodiphenyl ether (DBDPE), was obtained in the form of a brown-colored precipitate together with hydrogen bromide, bromine, and some lower brominated diphenyl ethers. The DEDPE may be separated from the reaction products to a great extent by neutralizing with aqueous NaOH, washing with water, and then filtering. The solid obtained was dried at 100 degrees C. and 10 mm Hg for two hours to give solvent-free DBDPE of 10–200µ particle size.

Although the process mentioned above could remove most of the impurities, the small amount of hydrogen bromide which was wrapped in the precipitates would cause the DBDPE to turn to a brown color when heated in the oven over along period of time. Many other proceses to purify the DBDPE from bromine contaminations by grinding it to small particle sizes and heating to a high temperature have been proposed. Examples of these processes are disclosed in U.S. Pat. No. 4,327,227, UK Patent Application GB No. 2,081,253, Japanese Patent Publication Nos. 78,116,332 and 78,116,334, French Patent Application FR No. 2,487,821, Japanese Publication No. 78 53,629, Japanese Publication No. 78, 21,129, and Ger. Offen. No. 2,984,149.

U.S. Pat. No. 4,327,227 discloses a process in which the thermally stable crude decabromodiphenyl ether is ground to reduce particles predominantly less than about 20 microns in diameter and thereafter heated at a temperature about 150°–300° C. for a time sufficient to effect substantial removal of the impurities therefrom. It is also disclosed therein that decabromodiphenyl ether is so insoluble in known solvents that purification by recrystallization is uneconomical and impractical.

U.S. Pat. No. 3,673,262 discloses a crystallization process for purification of gemdiphenylol alkanes and more especially the production of 2,2-bis (4-hydroxyphenyl) propane or bisphenol-A of a very high purity. The crystallization is effected by dissolving the above compound in a solvent and heating the resultant material to a temperature at least 5° C. above the atmospheric boiling point and at a pressure above the vapor pressure of the resultant material at that temperature. The process enables some difficulty soluble compounds to be dissolved efficiently in some solvents.

While the process disclosed in U.S. Pat. No. 3,673,262 is efficient, it is practically unsuitable for decabromodiphenyl ether, with impurities such as bromine and hydrogen bromide, since the decabromodiphenyl ether with these impurities is corrosive, especially when it is heated to an elevated temperature.

SUMMARY OF THE INVENTION

An object of the invention is to provide a crystallization process for purification of haloginated aromatic compounds from halogen and hydrogen halide contamination with a greater percentage of purity than conventional processes.

Another object of the present invention is to provide a process for purifying a brominated aromatic compound such as decabromodiphenyl ether from bromine and hydrogen bromide contamination by recrystallization.

The present invention provides a process for recrystallization of a brominated aromatic compound under pressure, for purifying it from the contamination by bromine, hydrogen bromide, etc., comprising the steps of: placing the brominated aromatic compound in a solvent or a combination of solvents selected from toluene, 1,2 dibromoethane, m-xylene, benzene, dichloromethane, chloroform, and 1,2-dichloroethane; adding into the resultant material a base or a combination of bases selected from pyridine, ethylene diamine, n-butylamine, tert-butylamaine, triethylamine, sodium ethoxide, sodium hydroxide, potassium hydroxide, sodium carbonate, and sodium bicarbonate; and heating the resultant material to a temperature above the atmospheric boiling point and at a pressure above the vapor pressure of the resultant material at that temperature.

According to the present invention, the solubility curves of decabromodiphenyl ether in toluene, 1,2-dibromoethane, m-xylene, benzene, dichloromethane, chloroform, 1,2-dichloroethane under pressure at the temperature higher than the atmospheric boiling point of the solvent are plotted as shown FIG. 1. It is noted that the solubility of decabromodiphenyl ether in those desirable solvents is relatively high within a temperature range of about 120° C.–174° C. The decabromodiphenyl ether which is difficultly soluble in the solvents becomes readily soluble when heated to the temperature higher than the atmospheric boiling point of the solvent. At the same time, the bromine and hydrogen bromide emitted from the dissolved decabromodiphenyl ether is neutralized by the organic or inorganic base, thereby minimizing the corrosion of the vessel, such as an autoclave, in which the process is carried out. In order to maintain a pressure higher than the vapour pressure of the resultant material, an inert gas such as nitrogen may be introduced into the vessel. Preferably, the amount of the solvent used is sufficient to dissolve all of the decabromodiphenyl ether. The amount of the base used may be 100 mol % to 200 mol % of the sum of the amount of hydrogen bromide and bromine present in the DBDPE. After the decabrodiphenyl ether is completely dissolved, the resultant material is cooled to provide pure decabromodiphenyl ether crystals. The crystals may then be washed with with acetone and milled to a size below 10 microns.

The process according to the present invention is most efficient for the purification of decabromodiphenyl ether having impurities mainly of hydrogen bromide and bromine. The process can also be employed for purification of other brominated aromatic compounds having impurities of hydrogen bromide and bromine.

BRIEF DESCRIPTION OF THE DRAWINGS

FIG. 1 is a diagram showing solubility curves of the decabromodiphenyl ether in various desirable solvents obtained by plotting the logarithm of the mol fraction of the decabromodiphenyl ether against $T_m/T$, where $T_m/T$ is the ratio of the melting point and the temperature, and the solvents employed in generating solubility curves 1 through 7 are respectively toluene, 1,2-Dibromoethane, m-Xylene, benzene, dichloromethane, chloroform, and 1,2-Dichloroethane; and FIGS. 2 and 3 are diagrams showing the results obtained from a thermogravimetric analysis and a differential scanning calorimatic analysis of the decabromodiphenyl ether crystal of Example 1.

EXAMPLE 1

4 Kg of crude DBDPE was placed in an autoclave (55 liter), then 40 liters of chloroform solution with 226.5 ml of an organic base, i.e pyridine, was added to the autoclave. Nitrogen is introduced to the autoclave with an initial pressure of about 1.5 kg/sq.cm at a temperature of 27 degrees C. The resultant mixture is stirred at a rate of 500 r.p.m. The heating rate was controlled by the circulation of a heating oil in the jacket of the autoclave. The average heating rate was 1.171 degrees C./min. After 128 min., the maximum pressure of the autoclave reached 15 kg/cm$^2$ at 172 degrees C. The stirring was stopped and the solution was cooled down naturally. The average coling rate was 0.19 degrees C./min. After 4 hours, gray-yellow color crystals were formed and isolated to give 3.73 kg of DBDPE (yield 93.25%). The melting point increased from 292-295 degrees C. before recrystallization to 298-304 degrees C. The thermal behaviors of DBDPE obtained by this method were determined by thermogravimetric (TGA) and differential scanning calorimetric (DSC) analyses and were shown in FIGS. 2 and 3 respectively.

EXAMPLE 2

3.5 kg of DBDPE which was obtained from example 1 was recrystallized again by the same method. Since it has been neutralized before, no organic base is added. 40 liter of chloroform was used as solvent. Once initial condition (1.5 kg/cm$^2$ and 23 degrees C.) was set, the solution was heated to 161 degrees C. under 13 kg/cm$^2$) at an average rate of 1.122° C./min. The average cooling rate was also 0.19° C./min. The crystal color was better than that of the first time recrystallization and the recovered yield was about 82%. The melting point of the crystal was also increased to 302°–304° C.

EXAMPLE 3

3 kg of crude DBDPE was mixed with 165 ml of pyridine and 38.87 liter of chloroform under an initial condition of 1.5 kg/cm$^2$ and 19° C. Then, the mixture was heated to achieve a final condition of 13.1 kg/cm$^2$ and 160° C. in 143 minutes. The cooling rate was 0.157° C./min. The weight of the crystal obtained was 2.592 kg and the yield of recovery was 86.4%. The melting point thereof was 302°–306° C.

Additional experiments were made for the recrystallization of the decabromodiphenyl ether by using different bases and solvents. Examples of them are shown in Table 1.

TABLE I

| Example | DBDPE | Solvent & Base | Pressure & Temp. | Product |
|---|---|---|---|---|
| 4. | 73.785 g | Ethylene diamine 5 ml<br>CHCl$_3$ 800 ml | 6 kg/sq. cm–14.3 kg/sq. cm<br>29° C.–165° C. | brown color<br>65.79 g, 89.16%<br>m.p. 302–304 C. |
| 5. | 73.785 g | Pyridine 4.5 ml<br>CHCl$_3$ 800 ml | same as above | light brown color<br>65.2 g, 88.37%<br>m.p. 303–306 C. |
| 6. | 80 g | toluene 0.8 liter<br>pyridine 5 ml | 9.5 kg/sq. cm<br>24–163° C. | 92.27 g<br>92.3%<br>m.p. 293–298° C. |
| 7. | 73.758 g | CHCl$_3$ 0.8 liter<br>tert-butylamine | 3–14 kg/sq. cm<br>15°–159° C. | 60.52 g<br>94.2% |
| 8. | 73.758 g | CHCl$_3$ 0.8 liter<br>triethylamine 5 ml | 3–14 kg/sq. cm<br>15°–159° C. | 68.97 g<br>93.47%<br>m.p. 293–298° C. |
| 9. | 50 g | CHCl$_3$ 500 ml<br>NaOH/ethanol<br>(0.2 N, 31,25 ml) | 80–125 psi<br>32°–150° C. | 43.3 g,<br>86%<br>cooling overnight<br>erosive iron |
| 10. | 50 g | CHCl$_3$ 700 ml<br>Na$_2$CO$_3$ sat. 100 ml | 75–300 psi<br>32°–150° C. | 44.5 g<br>89% |
| 11. | 140 g | CHCl$_3$ 1 liter<br>NaOH/ethanol (0.5 N, 100 ml) | 75 psi–280 psi<br>32°–150° C. | 103.54 g<br>73.95% |
| 12. | 80 g | toluene 0.8 liter<br>pyridine 5 ml | 3–9.5 kg/sq. cm<br>24–163° C. | 92.27 g<br>92.3%<br>m.p. 293° C.–298° C. |
| 13. | 73.785 g | CHCl$_3$ 0.8 liter<br>tert-butylamine 5 ml | 3–14 kg/sq. cm<br>20°–159° C. | 60.52 g<br>94.2%<br>m.p. 294–299° C. |
| 14. | 73.785 g | CHCl$_3$ 0.8 liter<br>triethylamine 5 ml | 3–14 kg/sq. cm<br>15–159° C. | 68.97%<br>93.47%<br>m.p. 293–298° C. |
| 15 | 73.785 g | CHCl$_3$ 0.8 liter<br>n-butylamine 5 ml | 4.8–14.8 kg/sq. cm<br>30°–160° C. | 69.24 g<br>93.85%<br>m.p. 294–299° C. |
| 16. | 73.785 g | CHCl$_3$ 0.8 liter<br>triethylamine 5 ml | 4.8–13.5 kg/sq. cm<br>30°–160° C. | 68.39 g<br>92.68%<br>m.p. 299–303° C. |
| 17. | 70 g | m-xylene 0.8 liter<br>pyridine 5 ml | 0–3 kg/sq. cm<br>20°–160° C. | 64.854 g<br>92.65%<br>m.p. 274–278° C. |

From Table I, it is seen that the lightest color of crystal was obtained by using NaOH and alcohol as base and chloroform as solvent. However, it is found that the combination can not alleviate the corrosion problem.

EXAMPLE 18

38.8 liter of chloroform, 0.033 kg of sodium hydroxide, 1.67 liter of ethanol and 150 ml of pyridine were added to 3 kg of crude DBDPE. The addition of an organic base, pyridine, avoided the corrosion of the autoclave and increased and solubility of DBDPE. The initial temperature and pressure (23° C. and 1.5 kg/cm$^2$) was increased to final conditions of 159 C and 14.5 kg/cm$^2$. Before the temperature of the solution began to drop, it was necessary to keep stirring to remove the hot spot effect on the bottom of autoclave. After cooling and washing with acetone, 2367 gm of light yellow crystal (87.9% yield) was obtained with a melting point of 300°–303° C.

With the invention thus explained, it is apparent that various modifications and variations can be made without departing from the scope of the present invention. It is therefore intended that the invention be limited as indicated in the appended claims.

I claim:

1. A process for purifying decabromodiphenyl ether from contamination by bromine and hydrogen bromide, comprising the steps of:

placing the decabromodiphenyl ether in a solvent or a combination of solvents selected from toluene, 1,2 dibromoethane, m-xylene, benzene, dichloromethane, chloroform, and 1,2-dichloroethane;

adding into the resultant mixture a base or a combination of bases selected from organic bases including pyridine, ethylene diamine, n-butylamine, tert-butylamine, triethylamine, and sodium ethoxide, and inorganic bases including sodium hydroxide, potassium hydroxide, aqueous sodium carbonate, and aqueous sodium bicarbonate;

heating the resultant mixture to a temperature above the atmospheric boiling point and at a pressure above the vapor pressure of the resultant material at that temperature, said temperature being within the range from about 120 degrees C to about 174 degrees C. and said pressure being within the range from about 5 kg/sq.cm to about 15 kg/sq.cm; and cooling the resultant mixture under pressure to recrystallize the decabromodiphenyyl ether.

2. A process as claimed in claim 1, wherein the amount of the base or combination of bases used is in the range from about 100 to about 200 mole % of the sum of moles of the bromine and hydrogen bromide present in the decabromodiphenyl ether.

3. A process as claimed in claim 1, further comprising the steps of: washing the recrystallized decabromodiphenyyl ether with acetone; and milling the washed, recrystallized decabromodiphenyyl ether to form crystals having size below 10 microns.

4. The process of claim 1, wherein said base or combination of bases is a liquid.

* * * * *